United States Patent [19]

Schülein et al.

[11] Patent Number: 5,776,757
[45] Date of Patent: Jul. 7, 1998

[54] FUNGAL CELLULASE COMPOSITION CONTAINING ALKALINE CMC-ENDOGLUCANASE AND ESSENTIALLY NO CELLOBIOHYDROLASE AND METHOD OF MAKING THEREOF

[75] Inventors: Martin Schülein, Copenhagen; Kirsten Bøegh Levring, Lyngby, both of Denmark

[73] Assignee: Novo Nordisk A/S, Bagsvaerd, Denmark

[21] Appl. No.: 452,943

[22] Filed: May 30, 1995

Related U.S. Application Data

[62] Division of Ser. No. 295,364, Aug. 24, 1994, abandoned, which is a continuation of Ser. No. 409,498, filed as PCT/DK89/00069 Mar. 22, 1989, abandoned.

[30] Foreign Application Priority Data

Mar. 24, 1988 [DK] Denmark .................... 1634/88
Mar. 24, 1988 [DK] Denmark .................... 1635/88

[51] Int. Cl.$^6$ .................... C12N 9/42; C12N 1/20; C12P 21/06; C07H 21/04
[52] U.S. Cl. .................... 435/209; 435/69.1; 435/252.3; 435/252.31; 435/252.33; 435/252.35; 435/254.11; 435/254.7; 435/320.1; 435/254.3; 435/911; 435/929; 536/23.2; 536/23.74
[58] Field of Search .................... 435/209, 320.1, 435/252.3, 254.11, 254.3, 252.33, 252.35, 252.31, 254.7, 911, 929, 69.1; 536/23.2, 23.74

[56] References Cited

U.S. PATENT DOCUMENTS

| 4,435,307 | 3/1984 | Barbesgaard et al. ............. 252/174.12 |
| 4,443,355 | 4/1984 | Murata et al. .................... 252/174.12 |
| 5,529,919 | 6/1996 | Knowles et al. .................... 435/209 |

FOREIGN PATENT DOCUMENTS

| 0 173 398 | 3/1986 | European Pat. Off. . |
| 0 220 016 | 4/1987 | European Pat. Off. . |
| 0 271 004 | 6/1988 | European Pat. Off. . |
| 2 095 275 | 9/1982 | United Kingdom . |

OTHER PUBLICATIONS

Buxton et al. (1985) Gene, 37, 207–214.
Koide et al. (1986) Agricultural and Biological Chemistry, 50, 233–237.

Primary Examiner—Robert A. Wax
Assistant Examiner—Elizabeth Slobodyansky
Attorney, Agent, or Firm—Steve T. Zelson; Elias J. Lambiris

[57] ABSTRACT

A cellulase preparation useful for reducing the harshness of cotton-containing fabrics and for reducing the rate at which such fabrics become harsh comprises about 40% or more (based on the total protein content) of an endoglucanase component with a pH optimum of about 7.5–10.0 with a high CMC-endoase activity and affinity towards cellulose and essentially no cellobiohydrolase activity. The cellulase composition is endogenous to a strain of Humicola, Myceliophthora, or Fusarium. A method for the recombinant production of said cellulase preparation is provided.

21 Claims, No Drawings

FUNGAL CELLULASE COMPOSITION CONTAINING ALKALINE CMC-ENDOGLUCANASE AND ESSENTIALLY NO CELLOBIOHYDROLASE AND METHOD OF MAKING THEREOF

This is a divisional of application Ser. No. 08/295,364 filed Aug. 24, 1994, now abandoned, which is a continuation of Ser. No. 07/409,498 filed Sep. 13, 1989, now abandoned, which is a continuation of PCT/DK89/00069 filed Mar. 22, 1989, the contents of which are incorporated herein by reference in their entirety.

FIELD OF INVENTION

The present invention concerns a cellulase preparation useful for reducing the harshness of cotton-containing fabrics and for reducing the rate at which such fabrics become harsh. The invention further relates to a detergent additive comprising the cellulase preparation, a detergent composition containing the cellulase preparation as well as a method of treating cotton-containing fabrics with the cellulase preparation.

BACKGROUND OF THE INVENTION

It is well known in the art that repeated washing of cotton-containing fabrics generally causes a pronounced, unpleasant harshness in the fabric, and several methods for overcoming this problem have previously been suggested in the art. For example U.S. Pat. No. 1,368,599 of Unilever Ltd. teaches the use of cellulytic enzymes for reducing the harshness of cotton-containing fabrics. Also, U.S. Pat. No. 4,435,307 (of Novo Industri A/S) teaches the use of a cellulytic enzyme derived from *Humicola insolens* as well as a fraction thereof, designated $AC_xI$, as a harshness reducing detergent additive. Other uses of cellulytic enzymes mentioned in the art involve soil removal from and colour clarification of fabric (cf. for instance EP 220 016).

Although the use of cellulytic enzymes for harshness reduction of cotton-containing fabrics was suggested and demonstrated nearly 20 years ago the mechanism of this process has not been elucidated and is still now known in detail. Among other things, this is due to the multiplicity of the enzymes and the enzyme-catalyzed reactions involved. As a matter of fact, cellulases generated in nature e.g. by microbial species are indeed complex mixtures of cellulytic enzymes. Accordingly, the conversion of naturally occurring materials, like cotton, catalyzed by cellulases is exceedingly difficult to analyze in detail.

Due to these circumstances the practical exploitation of enzymatic harshness reduction and prevention, however desirable, has not be come widespread and of great practical utility: it is difficult to optimise production of multiple enzyme systems and thus to implement industrial cost-effective production of cellulytic enzymes, and their actual use has been hampered by difficulties arising from the need to apply rather large quantities of the cellulytic enzymes to achieve the desired reduction and prevention of the harshness of cotton fabrics: for instance, addition of large quantities of the enzymes to detergent compositions is not compatible with the optimal function of other ingredients in the detergent formulation nor is the addition of very large quantities of enzymes to the detergent composition in the interest of e.g. consumer safety.

SUMMARY OF THE INVENTION

We have found that, surprisingly, enzymatic softening of cellulose-containing fabrics, primarily cotton-containing fabrics, as well as soil removal and colour clarification may be provided by a cellulase fraction enriched in endoglucanase activity.

Accordingly, the present invention relates to a cellulase preparation which comprises above about 40% (on the basis of total protein as determined from the OD at 280 nm) of an endoglucanase component which exhibits a CMC-endoase activity (as defined below) of above about 5 CMC-endoase units per mg of total protein and a cellulose affinity viscosity unit (CAVU) activity (as defined below) of above about 50% under alkaline conditions.

More specifically, the present invention relates to a cellulase preparation, which comprises at least 50% (by weight of the total cellulase content) of a substantially homogenous endoglucanase component which exhibits a CMC-endoase activity of at least 5 CMC-endoase units per mg of total protein and a CAVU activity of at least 50% under alkaline conditions.

In the present context, the term "CMC-endoase activity" refers to the endoglucanase activity of the endoglucanase component in terms of its ability to degrade cellulose to glucose, cellobiose and triose, as determined by a viscosity decrease of a solution of carboxymethyl cellulose (CMC) after incubation with the cellulase preparation of the invention, as described in detail below.

The term "CAVU activity" refers to the affinity of the endoglucanase components towards cellulose. This affinity may conveniently be determined by measuring the CMC-endoase activity of a solution of the cellulase preparation of the invention under certain standard conditions as specified in detail below before and after incubation of the enzyme solution with a cellulose-containing material. The affinity of the endoglucanase component towards cellulose may subsequently be expressed in percent CAVU units which is calculated as the difference between the CMC-endoase activity of the untreated and cellulose-treated enzyme solution divided by the activity of the untreated solution and multiplied by 100.

It should be noted that the endoglucanase component present in the cellulase preparation of the invention is one which is active (in terms of CMC-endoase and CAVU activity) under alkaline conditions. More specifically, the endoglucanase component is one which has a pH optimum at a pH of about 7.5–10. Contrary to several known cellulases which are active at an acid pH and relatively inactive at alkaline pH values, this characteristic makes the cellulase preparation of the present invention particularly useful for washing purposes, in particular as an ingredient in a detergent composition, as washing of clothes is typically conducted under alkaline conditions due to the alkalinity of most washing detergents. Alkalophilic cellulases are known, e.g. from EP 271 004, but cellulase preparations containing an endoglucanase component which exhibits a high affinity to cellulose under alkaline conditions are believed to be novel.

The finding that a particular endoglucanase component of cellulase is responsible for the softening of cotton-containing fabrics is of considerable practical significance: it permits a cost-effective production of fabric-softening cellulytic enzymes, e.g. by employing recombinant DNA techniques for producing the active component, it makes the actual effective application of these enzymes feasible and it permits an identification of cellulytic enzymes with a high affinity to cellulose for use as fabric softeners.

DETAILED DISCLOSURE OF THE INVENTION

Preferred cellulase preparations of the invention are those in which the endoglucanase component exhibits a CMC-endoase activity of above about 10, in particular above about 15, CMC-endoase units per mg of total protein. In particular, the endoglucanase component exhibits a CMC-endoase activity of about 50 or more CMC-endoase units per mg of total protein. Other preferred cellulase preparations are those in which the endoglucanase component exhibits a CAVU activity of above about 65%, especially above about 75%. Particularly favoured cellulase preparations are those in which the endoglucanase component exhibits a high CMC-endoase activity concomitantly with a high CAVU activity.

The CMC-endoase (endoglucanase) activity can be determined from viscosity decrease of CMC, as follows:

A substrate solution is prepared, containing 35 g/l CMC (Hercules 7 LFD) in 0.1M tris buffer at pH 9.0. The enzyme sample to be analyzed is dissolved in the same buffer.

10 ml substrate solution of 0.5 ml enzyme solution are mixed and transferred to a viscosimeter (e.g. Haake VT 181, NV sensor, 181 rpm), thermostated at 40° C.

Viscosity readings are taken as soon as possible after mixing and again 30 minutes later. The amount of enzyme that reduces the viscosity to one half under these conditions is defined as 1 unit of CMC-endoase activity.

The affinity of endoglucanases towards cellulose fibers (the "CAVU-activity") may be determined by measuring the binding of the enzymes to a cellulose-containing material under alkaline conditions. This activity measurement may be carried out as follows:

First the CMC-endoase activity is determined as described above. Then about 50 CMC-endoase units in 10 ml buffer (0.1M tris pH 9.0) is applied to 2.5 g Avicel (Merck Art. 2330) in a 25 ml beaker. The resulting suspension is stirred for 30 minutes at room temperature by using a magnetic stirrer and then centrifuged for 10 minutes at 3000 rpm whereupon the CMC-endoase activity of the resulting supernatant is measured. Finally the % CAVU activity is calculated as the difference between the total CMC-endoase activity of the original solution and the supernatant divided by the total CMC-endoase activity and multiplied by 100.

In accordance with the principles of the present invention, it is an advantage that the cellulase preparation be as purified as possible, i.e. that its content of the endoglucanase component be as high as possible, so that a smaller quantity of the preparation is required for the softening of cotton-containing fabrics than is the case with known cellulases. Particularly preferred cellulase preparations of the invention are those which comprise about 90% or more of the appropriate endoglucanase component.

Cellulase preparations according to invention may be obtained from plants and microorganisms where endoglucanases may be present in small quantities together with a wide variety of other cellulytic enzymes. Examples of bacteria and fungi from which potentially interesting cellulytic enzymes may be isolated are listed in GB 2094826A, p. 3, line 35, to p. 6, line 7. To obtain cellulase preparations of the invention, crude cellulases must be subjected to extensive purification procedures according to principles known in the art. For industrial production of the cellulase preparations according to the invention, it is preferred to employ recombinant DNA techniques or other techniques involving adjustments of fermentations, mutation of the microorganisms involved to ensure overproduction of the desired enzymatic activities, or development of methods for large-scale purification of the endoglucanase component. Such methods and techniques are known in the art and may readily be carried out by persons skilled in the art. In the following examples some specific examples are given of purification techniques that may be used to furnish enzymes to be employed according to the method of the invention. It appears from the examples that ion-exchange chromatography, size exclusion chromatography, and fractionated precipitation are techniques which may be used to great advantage.

The endoglucanase component present in the cellulase preparation of the invention may be one producible by a fungus. We have found that cellulose preparations with a high CMC-endoase and CAVU activity may readily be isolated from species of Humicola such as *Humicola insolens* e.g strain DSM 1800, deposited on 1 Oct. 1981 at the Deutsche Sammlung von Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure (the Budapest Treaty).

Accordingly, the present invention further relates to a cellulase preparation containing a cellulase producible by cultivation of a strain of *H. insolens*, the cellulase comprising above about 40%, preferably above 90% (on the basis of the total protein, determined from the OD at 280 nm) of an endoglucanase component with the following properties:

a) approximate molecular weight of about 65 kD (determined by SDS-PAGE)
b) isoelectric point of about 8.5–9.5
c) endoglucanase activity above about 50 CMC-endoase units/mg of total protein
d) essentially no cellobiohydrolase activity
e) immunological reaction with polyspecific antibody raised against a cellulase derived from *Humicola insolens* DSM 1800

(cellobiohydrolase activity being defined as the activity towards cellobiose p-nitrophenyl, determined as described below).

Another preferred microorganism from which enzymes that may be employed according to the invention may be isolated are strains of Fusarium, *Fusarium oxysporum* being preferred e.g. the strain DSM 2672, deposited on 6 Jun. 1983 at the Deutsche Sammlung von Mikroorganismen in accordance with the provisions of the Budapest Treaty.

A further preferred microorganism from which the above mentioned enzymes may be isolated is a strain of Myceliopthora, *Myceliopthora thermophila* being particularly preferred.

Also preferred as sources of enzymes to be employed according to the invention are species of Erwinia, e.g. strains of *Erwinia chrysanthermi* described by M. H. Boyer et. al. in European Journal of Biochemistry, vol. 162, page 311–316 (1987).

Other preferred sources of enzymes are species of Microbispora, e.g. *Microbispora bispora*, species of Neocallimastix, such as *Neocallimastix frontalis*, species of Piromonas, e.g. *Piromonas communis*, or species of Robillarda.

The endoglucanase component may also be one producible by a bacterium, e.g. a species of Streptomyces of Clostridium, such as *Clostridium thermocellum*.

The endoglucanase component may furthermore be one which is producible by a method comprising cultivating a host cell transformed with a recombinant DNA vector which carries a DNA sequence encoding said endoglucanase component as well as DNA sequences encoding functions permitting the expression of the DNA sequence encoding the endoglucanase component, in a culture medium under conditions permitting the expression of the endoglucanase component and recovering the endoglucanase component from the culture.

A DNA fragment encoding the endoglucanase component may, for instance, be isolated by establishing a cDNA or genomic library of a cellulase-producing microorganism, such as one of the organisms mentioned above, and screening for positive clones by conventional procedures such as by hybridization to oligonucleotide probes synthesized on the bases of the full or partial amino acid sequence of the endoglucanase, or by selecting for clones expressing the appropriate enzyme activity (i.e. CMC-endoase and CAVU activity as defined above), or by selecting for clones producing a protein which is reactive with an antibody against a native cellulase (endoglucanase) component.

Once selected, the DNA sequence may be inserted into a suitable replicable expression vector comprising appropriate promotor, operator and terminator sequences permitting the endoglucanase to be expressed in a particular host organism, as well as an origin of replication enabling the vector to replicate in the host organism in question.

The resulting expression vector may then be transformed into a suitable host cell, such as a fungal cell, a preferred example of which is a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238,023 (of Novo Industri A/S), the contents of which are hereby incorporated by reference.

Alternatively, the host organisms may be a bacterium, in particular strains of Streptomyces and Bacillus, and *E. coli*. The transformation of bacterial cells may be performed according to conventional methods, e.g. as described in T. Maniatis et al., *Molecular Cloning: A Laboratory Manual*, Cold Spring Harbor, 1982.

The screening of appropriate DNA sequences and construction of vectors may also be carried out by standard procedures, cf. T. Maniatis et. al., op. cit.

The medium used to cultivate the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide endoglucanases of a high purity.

The cellulase preparation of the invention may conveniently be added to cotton-containing fabrics together with other detergent materials curing soaking, washing or rinsing operations. Accordingly, in another aspect, the invention relates to a detergent additive comprising above about 40% (on the basis of total protein as determined from the OD at 280 nm) of an endoglucanase component which exhibits a CMC-endoase activity (as defined above) of above about 5 CMC-endoase units per mg of total protein and a CAVU activity (as defined above) of above about 50% under alkaline conditions. The detergent additive may suitably be in the form of a non-dusting granulate, stabilized liquid or protected enzyme. Non-dusting granulates may be produced e.g. according to U.S. Pat. Nos. 4,106,991 and 4,661,452 (both to Novo Industri A/S) and may optionally be coated by methods known in the art. Liquid enzyme preparations may, for instance, be stabilized buy adding a polyol such as propylene glycol, a sugar or sugar alcohol, lactic acid or boric acid according to established methods. Other enzyme stabilizers are well known in the art. Protected enzymes may be prepared according to the method disclosed in EP 238, 216.

The detergent additive may suitably exhibit a CMC-endoase activity (as defined above) of 500–10,000 CMC-endoase units per gram of the additive. It will be understood that the detergent additive may further include one or more other enzymes, such as protease, lipase or amylase, conventionally included in detergent additives.

In a still further aspect, the invention relates to a detergent composition comprising above about 40% (on the basis of total protein as determined from the OD at 280 nm) of an endoglucanase component which exhibits a CMC-endoase activity (as defined above) of above about 5 CMC-endoase units per mg of total protein and a CAVU activity (as defined above) of above about 50% under alkaline conditions.

Detergent compositions of the invention additionally comprise surfactants which may be of the anionic, non-ionic, cationic, amphoteric, or zwitterionic type as well as mixtures of these surfactant classes. Typical examples of anionic surfactants are linear alkyl benzene sulfonates (LAS), alpha olefin sulfonates (AOS), alcohol ethoxy sulfates (AES) and alkali metal salts of natural fatty acids.

Detergent compositions of the invention may contain other detergent ingredients known in the art as e.g. builders, bleaching agents, bleach activators, anti-corrosion agents, sequestering agents, anti soil-redeposition agents, perfumes, enzyme stabilizers, etc.

The detergent composition of the invention may be formulated in any convenient form, e.g. as a powder or liquid. The enzyme may be stabilized in a liquid detergent by inclusion of enzyme stabilizers as indicated above. Usually, the pH of a solution of the detergent composition of the invention will be 7–12 and in some instances, 7.0–10.5. Other detergent enzymes such as proteases, lipases or amylases may be included the detergent compositions of the invention, either separately or in a combines additive as described above.

The softening, soil removal and colour clarification effects obtainable by means of a cellulase preparation of the invention generally require a concentration of the cellulase preparation in the washing solution corresponding to an endoglucanase activity of 5–200 CMC-endoase units per liter. The detergent composition of the invention is typically employed in concentrations of 0.5–20 g/l in the washing solution. Consequently, the cellulase concentration of the detergent composition of the invention is about 0.3–400 CMC-endoase units per gram. In general, it is most convenient to add the detergent additive in amounts of 0.1–5% w/w or, preferably, in amounts of 0.2–2% of the detergent composition.

In a still further aspect, the present invention relates to a method of reducing the rate at which cotton-containing fabrics become harsh or of reducing the harshness of cotton-containing fabrics, the method comprising treating cotton-containing fabrics with a cellulase preparation as described above. The method of the invention may be carried out by treating cotton-containing fabrics during washing. However, if desired, treatment of the fabrics may also be carried out during soaking or rinsing or simply by adding the cellulase preparation to water in which the fabrics are or will be immersed.

The present invention is described in further detail with reference to currently preferred embodiments in the following examples which are not intended to limit the scope of the invention in any way.

EXAMPLES

Example 1

Purification and washing trails using cellulases from *Humicola insolens*

Fractionation of *H. insolens* cellulase

Cellulase is produced by cultivation of *Humicola insolens* DSM 1800, according to U.S. Pat. No. 4,435,307, Example 6. Crude cellulase is be recovered from the culture broth by filtration on diatomaceous earth, ultrafiltration and freeze-drying of the retentate, cf. Examples 1 and 6 of U.S. Pat. No. 4,435,307.

The crude cellulase is purified on DEAE-Sephadex and separated by anion-exchange chromatography on DEAE-Sepharose at pH 10. The non-absorbed fraction (designated F1) has a softening effect (per mg of protein) which is about 2 times that of the crude cellulase or of the $AC_xI$ fraction of U.S. Pat. No. 4,435,307).

After concentration, F1 is fractionated by a two-step $(NH_4)_2SO_4$ precipitation: the precipitate at 25% saturation is discarded, after which the precipitate at 55% saturation is collected and designated F1P1. It has an approximately 3 times higher softening power than the crude cellulase.

F1P1 is then separated by size chromatography (Sephacryl). The protein elutes in 3 main peaks, C1, C2, C3. The C1 elutes with an apparent MW of about 80,000. C2 with a MW of about 65,000 and C3 with a MW of about 40,000. The main activity of C1 is the activity against PNP-Cellobiose. The main activity in C2 is the endoglucanase activity. The C3 fraction contains mainly exoglucanase activity. Thus, of the three fractions, only F1P1C2 is within the scope of the invention. It has about 5 times the softening effect of the crude cellulase.

F1P1C2 contains about 50% of a single protein, designated Endoglucanase I. This may be further purified by preparative size chromatography, e.g. on a TSK column.

Below, the crude cellulase and the various fractions are compared according to softening power (in washing testsperformed as described below), endoglucanase activity (CMC-endoase, as defined above) and content of endoglucanase I (in % of total protein, determined by a method indicated later). Each of these is expressed in relation to the total protein amount, determined by the OD at 280 nm. The figures indicate typical results. It is believed that some of the measured activities are negatively influenced by protease impurity.

| Cellulase preparation | CMC-endoase | % Endo I of protein | Softening power relative to protein amount |
|---|---|---|---|
| Prior art: | | | |
| crude cellulase | | | 1x |
| $AC_xI$ (U.S. Pat. No. 4,435,307) | 4.5 | below 10 | 1x |
| Fractions: | | | |
| F1 | 6 | 15 | 2x |
| F1P1 | 12 | 25 | 3x |
| F1P1C2 (invention) | 19 | 50 | 5x |

As indicated, fractionation of crude cellulase to F1, F1P1 and finally F1P1C2 leads to a progressively increasing softening power (per amount of protein). Soil removal increases similarly. The improved preparations of the invention may be distinguished from prior-art preparations by the increased endoglucanase activity (CMC-endoase/mg of total protein and by the increased content of Endoglucanase I. The crude cellulase was found to exhibit a CAVU activity of 78%. The CAVU activities of the fractions were in the range of 75–92%.

Enzyme-chemical characterization of "Endoglucanase I"

SDS-PAGE and isoelectric focusing (IEF) with marker proteins are convenient methods for determining molecular weight (MW) and isoelectric point (pI), respectively. According to these methods, Endoglucanase I has a MW of about 65 kD and pI of about 8.5–9.5. The F1P1C2 fraction described above contains about 50% of this cellulase, and it contains a minor amount of protein with a MW of about 50 kD and a pI of about 5.8. Because of the high degree of glycosylation the MW in the SDS gel and the pI may vary due to difference in fermentation conditions and type of buffer during purification.

The enzyme activity was measured as the CMC-endoase and CAVU activity as defined above. In each case the above F1P1C2 preparation was used to estimate the properties of pure Endoglucanase I.

a) endoglucanase activity of above 50 CMC-endoase/mg of total protein.

b) essentially no cellobiohydrolase activity (below 0.5 PNP-Cel/mg).

Endoglucanase I is glycosylated, as seen by binding to Con-A.

Immunochemical characterization

Antiserum against proteins may be raised for example by immunizing rabbits according to the procedure described in N. Axelsen et al. in: *A Manual of Quantitative Immunoelectrophoresis*, Blackwell Scientific Publications, 1973, Chapter 23. Purified immunoglobulins may be obtained from the antisera, for example by salt precipitation $((NH_4)_2 SO_4)$, followed by dialysis and ion exchange chromatography, e.g. on DEAE-Sephadex.

Immunochemical characterization of proteins may be conducted either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2,).

The fractionated cellulase preparations of the invention (F1, F1P1, F1P1C2) show immunological reaction with serum raised against the crude cellulase from DSM 1800, as well as serum raised against F1P1C2.

Cellobiohydrolase activity (PNP-Cel)

Cellobiohydrolase activity can be measured with PNP-Cellobiose, p-Nitrophenyl-beta-D-cellobioside (Sigma N-5759). The activity is determined as µmole released nitrophenyl per minute at 37° C. at pH 7.0.

Determination of Endoglucanase I by size chromatography

Analytical HPLC is performed on a 220 ml column of TSK SW 3000 with flow rate 5 ml/min of 0.1M sodium acetate buffer, pH 6.1 C1 elutes at 35 minutes, C2 at 37 minutes (as bovine serum albumin), and C3 at 40 minutes.

Purification of cellulase

A total of 228,000 CMC-endoase of crude cellulase prepared as described in Example 6 of U.S. Pat. No. 4,435,307 was used. It was diluted in 20 l buffer at pH 10.5 using ethanol amine, and treated with 25 g DEAE-Sephadex at 4° C. for 4 hours. The non-bound protein was concentrated and freeze-dried. This corresponds to the $AC_xI$ fraction described in U.S. Pat. No. 4,435,307.

After concentration on a Millipore Pelicon cell with a MW cut-off at 10,000, 4000 ml of $AC_xI$ was obtained, containing 215,000 endoase. This was subjected to anion exchange chromatography at pH 10.5.

Column chromatography was performed on DEAE-Sepharose CL in a 10×25 cm column equilibrated with buffer 20 nM Ethanolamine pH 10.5, flow rate 500 ml per hour.

The non-bound material in a total volume of 10,000 ml was adjusted to pH 7.0 and concentrated on a Millipore Pelicon cell with MW cut-off at 10,000.

The result was a fraction of 1300 ml, designated F1. This was first saturated with 20% w/v ammonium sulphate and the precipitate was discarded, followed by 35% w/v ammonium sulphate. The new precipitate was collected by centrifugation and solubilized in water to a total volume of 130 ml, designated F1P1.

Two times 40 ml of this was applied to Sephacryl S-200 size chromatography: Buffer 100 mM ammonium acetate pH 6.5, flow rate 200 ml per hour, size of the column 5×85 cm. The protein eluted in 3 main peaks: C1, C2, C3.

| Result | Volume | Protein mg per ml | Endoase per ml | PNPCEL per ml |
|---|---|---|---|---|
| $AC_x1$ | 4000 | 12 | 54 | 1.3 |
| C1 | 410 | 2.8 | 22 | 8.8 |
| C2 | 265 | 5.3 | 100 | 0.5 |

Softening effect in washing trials

Experimental conditions:

Washing machine: Terg-O-tometer

Temperature: 40° C.

Time: 15 minutes

Agitation: 100 rpm

Detergent: 5 g/l "Gron Biotex" from Bluemoller-A/S Denmark pH: Adjusted to pH 9.0

Water hardness: Tap water, approx. 18° dH

Test material: Cotton terry cloth, 19 cm×19 cm A/S Georg Jensen Damaskvæveriet prepared as described below Cloth/liquid ratio: 2 swatches/1 liter per bucket, 38/1

Cellulase: See below

Cellulase dosages: In the range 2.5 to 125 mg protein/l

Rinsing: the swatches were rinsed in a household machine (Miele W 761). The rinsing was followed by a spin drying at 900 rpm for 38 seconds.

Drying: Line drying

Number of washings: 1

Preparation of test material 100 swatches or about 1.9 kg were prewashed in a household washing machine (Miele W 761). Wash program was "Kulort vask 60° C., kort", i.e. a one-cycle European wash. The swatches were spin-dried at 1200 rpm at the end of each wash cycle, but not dried between the washings. After 20 washings the swatches were line dried.

Different cellulase preparations were used, and the softness of the treated swatches was compared to find relative dosage of the various preparations needed to give the same softening effect.

Results

| Cellulase | Softening power relative to protein amount |
|---|---|
| Crude cellulase | (taken as basis) |
| $AC_xI$ | around 1 × basis |
| F1 | around 2 × basis |
| F1P1 | around 3 × basis |
| F1P1C2 | around 5 × basis |

It appears that the three fractionated preparations (F1, F1P1, F1P1C2)show improved softening effect.

Example 2

Purification and washing trials using cellulases from *Fusarium oxysporum*

*Fusarium oxysporum* strain J 79 (deposit No. DSM 2672) was cultivated at 30° C. on an agar substrate containing the following nutrients:

| Yeast extract Difco | 4 g |
|---|---|
| $K_2HPO_4$ | 1 g |
| $MgSO_4.7H_2O$ | 0.5 g |
| Glucose | 15 g |
| Distilled water | 1000 ml |
| Agar | 15 g |

The culture was incubated for 6 days in a Fernbach flask whereupon the resulting spores were transferred to a 500 l stainless steel fermentation tank containing 300 liters of pre-fermentation substrate of the following composition:

| Corn steep liquor | 23.3 g per liter |
|---|---|
| Glucose | 24.0 g per liter |
| $CaCO_3$ | 5.0 g per liter |
| Pluronic | 0.1 ml per liter. |

(the pH of the medium was adjusted to 5.5 with $H_3PO_4$ before being sterilization at 121° C. for 60 min). The resulting culture was aerated using 300 liters of air per minutes at a pressure of 0.5 atmosphere.

After growth for 23 hours at 30° C. 150 liters of the dense culture obtained was used to seek a fermentation production tank containing 1500 l of a medium sterilized at pH 6.5 at 121° C. for 60 minutes and containing the following ingredients:

| Corn steep liquor | 20 g per liter |
|---|---|
| Cellulose powder, Diacell | 40 g per liter |
| $KH_2PO_4$ | 10 g per liter |
| $CaCO_3$ | 5 g per liter |
| $NH_4NO_3$ | 10 g per liter |
| $MgSO_4.7H_2O$ | 1 g per liter |
| Pluronic | 0.1 ml per liter. |

The fermentation mixture was aerated using 750–1500 liters of air per minute at a pressure of 0.5 atmosphere and stirred at a rate of 200 rpm. The temperature was 30° C. and the pH kept at 6.0 by addition of 4.9% phosphoric acid during the first 40 hours of fermentation time and, after 70 hours, kept above 5.0 by addition of diluted calcium carbonate. After 108 hours the fermentation was stopped, the culture was cooled to 5° C., the culture broth was removed by filtration, and, finally, the filtrate was freeze dried after concentration by ultrafiltration.

10 grams of a freeze dried cellulase powder obtained (exhibiting a total CMC-endoase activity of 18.118 units)

was subjected to chromatography on 350 ml of DEAE-Sepharose type CL-6B purchased from Pharmacia Company using 600 ml of a linear gradient of 1M NaCl in 50 mM Tris buffer at pH 7. Fractions (20 ml) from the chromatography were pooled, concentrated on an Amicon ultrafiltration membrane reactor equipped with a membrane type GR 81 PP with a MW cut-off at 10 kDalton purchased from Danish Sugar company and finally analyzed as indicated in the table below:

| Pool | ml | E.280 | Total mg protein | Endoase per ml | Total endoase | Endoase/ mg protein |
|---|---|---|---|---|---|---|
| 1 | 58.8 | 52.2 | 3070 | 329 | 19,369 | 6.3 |
| 2 | 18.8 | 15.2 | 286 | 14 | 254 | 0.9 |
| 3 | 24.2 | 6.0 | 145 | 22 | 527 | 3.7 |
| 4 | 33 | 40 | 1320 | 11 | 363 | 0.3 |

Pool 1, which did not bind to the anion exchange column, was found to exhibit a CAVU activity of 87%. In SDS PAGE it showed a main band with a molecular weight of 80 kDalton. When tested in washing trials (as described in Example 1) using a simple detergent of pH 8 and a CMC-endoase activity from 60 units per liter of washing liquor the protein in this band was found to exhibit an excellent softening effect.

Example 3

Purification and washing trials using cellulases from *Myceliophthora thermophile*

The stain CBS 117.65 (*Myceliopthora thermophile*) was cultivated at 37° C. on an agar substrate having the following composition:

| Yeast extract Difco | 4 g |
|---|---|
| K$_2$HPO$_4$ | 1 g |
| MgSO$_4$.7H$_2$O | 0.5 g |
| Glucose | 15 g |
| Distilled water | 1000 ml |
| Agar | 15 g |

The culture was incubated for 6 days in a Fernbach flask. Then the spores were transferred to a 500 l stainless steel fermentation tank containing 280 liters of a medium containing the following constituents:

| Soybean meal | 28.9 g per liter |
|---|---|
| K$_2$HPO$_4$ | 2.1 g per liter |
| CaCO$_3$ | 5.0 g per liter |
| Pluronic | 0.4 ml per liter |
| Glucose | 4.3 g per liter |
| Citric acid | 6.7 g per liter. |

(The glucose and the citric acid of the medium were sterilized separately at 123° C. for 60 minutes. pH of the medium was adjusted to 5.5 with H$_3$PO$_4$ before sterilization at 123° C. for 90 min). Sterile air was passed through the resulting culture at a pressure of 0.5 atmospheres and at a rate of 200 liters per min.

After growth for 48 hours at 37° C. 120 liters of the dense culture obtained was used to seed an enzyme production tank containing 1500 liters of a substrate of the following composition:

| Soybean meal | 30 g per liter |
|---|---|
| Cellulose powder, Solkafloc | 20 g per liter |
| KH$_2$PO$_4$ | 2 g per liter |
| CaCO$_3$ | 4.5 g per liter |
| Pluronic | 0.17 ml per liter. |

(the pH of the medium was adjusted to 6.5 with NaOH/H$_3$PO$_4$ before sterilization at 123° C. for 90 min).

The culture was aerated at a rate of 1500 liters per minutes under the pressure of 0.5 atmosphere and was stirred at a rate of 250 rpm. The fermentation was allowed to proceed for 64 hours at 37° C. whereupon the culture was chilled to 5° C. and filtered to provide a filtrate which was freeze dried after concentration by ultrafiltration.

5 grams of the cellulase powder (found to exhibit a CMC-endoase activity of 6176 units per gram) was fractionated using a Sephacryl type S 200 column material and a 0.1M sodium acetate buffer of pH 6.1. Fractions of 15 ml were collected, analyzed by SDS electrophoresis and pooled according to the protein pattern of the gels as follows:

pool 1 475 ml, SDS gel: 100, 90 kDalton
pool 2 500 ml, SDS gel: 70, 50, 45 kDalton
pool 3 400 ml, SDS gel: 70, 60, 50, 45 kDalton
pool 4 410 ml, SDS gel: 45, 30 kDalton
pool 5 310 ml, SDS gel: 65, 50, 18 kDalton
pool 6 850 ml, SDS gel: 65, 50, 40, 18 kDalton The pools were then concentrated on a Amicon membrane reactor with a ultrafiltration membrane type GR 81 PP purchased from the Danish Sugar Factories, MW cut-off at 10 kDalton, and they were subsequently analyzed as follows:

| Pool | ml | E.280 | Total mg protein | Endoase per ml | Total endoase | Endoase/ mg protein |
|---|---|---|---|---|---|---|
| 1 | 13.0 | 17.6 | 229 | 74 | 956 | 4.2 |
| 2 | 18.3 | 23.1 | 423 | 372 | 6803 | 16.1 |
| 3 | 11.8 | 16.2 | 191 | 139 | 1645 | 8.6 |
| 4 | 20.0 | 18.3 | 366 | 196 | 3929 | 10.7 |
| 5 | 11.6 | 22.6 | 262 | 286 | 3318 | 11.6 |
| 6 | 21.0 | 20.0 | 420 | 252 | 5292 | 12.6 |

The following CAVU activities were measured:

| Pool 2 | 23% CAVU |
|---|---|
| Pool 3 | 22% CAVU |
| Pool 4 | 13% CAVU |
| Pool 5 | 75% CAVU |
| Pool 6 | 88% CAVU |

When tested in washing trials (as described in Example 1) using a simple detergent of pH 8 and a CMC-endoase activity of 180 units per liter of washing liquor pool 5 and 6 only were found to exhibit an excellent softening effect. In contract Pool 2 which exhibits a CMC-endoase activity of 16 units/mg was found not to give rise to any softening when tested.

We claim:

1. A method for producing a cellulase preparation which comprises a substantially homogeneous endoglucanase, comprising:
   (a) introducing a recombinant DNA vector carrying a first DNA sequence encoding the endoglucanase operably linked to control sequences permitting the expression of said first DNA sequence into a host cell;
   (b) cultivating the host cell in a culture medium under conditions permitting the expression of the endoglucanase; and (c) recovering the endoglucanase from the culture medium;

wherein the endoglucanase is endogenous to a strain of Myceliophthora, Fusarium or Humicola and (i) has a pH optimum of about 7.5–10.0;

(ii) exhibits a carboxymethylcellulose (CMC) endoase activity of at least about 10 CMC-endoase units per mg of total protein;

(iii) exhibits a cellulose affinity viscosity unit (CAVU) activity of at least about 50% at a pH of 7.0–12.0; and (iv) has essentially no cellobiohydrolase activity.

2. The method according to claim 1, wherein the host cell is an Aspergillus cell.

3. The method according to claim 2, wherein the host cell is an *Aspergillus oryzae* or *Aspergillus niger* cell.

4. The method according to claim 1, wherein the host cell is a bacterial cell.

5. The method according to claim 4, wherein the host cell is a Bacillus, Streptomyces or *E. coli* cell.

6. The method according to claim 1, wherein the endoglucanase exhibits a CMC-endoase activity of at least about 15 CMC-endoase units per mg of total protein.

7. The method according to claim 6, wherein the endoglucanase exhibits a CMC-endoase activity of at least about 50 CMC-endoase units per mg of total protein.

8. The method according to claim 1, wherein the endoglucanase exhibits a CAVU activity in excess of about 65%.

9. The method according to claim 8, wherein the endoglucanase exhibits a CAVU activity in excess of about 75%.

10. The method according to claim 1, wherein the fungus is Humicola.

11. The method according to claim 10, wherein the fungus is *Humicola insolens*.

12. The method according to claim 1, wherein the fungus is Fusarium.

13. The method according to claim 12, wherein the fungus is *Fusarium oxysporum*.

14. The method according to claim 1, wherein the fungus is Myceliophthora.

15. The method according to claim 1, wherein the endoglucanase has a molecular weight of about 65 kilodaltons as determined by denaturing gel electrophoresis.

16. The method according to claim 15, wherein the fungus is Humicola.

17. The method according to claim 16, wherein the fungus is *Humicola insolens*.

18. The method according to claim 1, wherein the endoglucanase has (e) an isoelectric point of about 8.5–9.5; and (f) an immunological reaction with a polyspecific antibody raised against cellulase derived from *Humicola insolens* DSM 1800.

19. The method according to claim 1, wherein the endoglucanase has a molecular weight of about 80 kilodaltons as determined by denaturing gel electrophoresis.

20. The method according to claim 19, wherein the fungus is Fusarium.

21. The method according to claim 20, wherein the fungus is *Fusarium oxysporum*.

* * * * *